United States Patent
Hall et al.

(10) Patent No.: US 10,383,576 B2
(45) Date of Patent: Aug. 20, 2019

(54) SYNTHETIC APERTURE PHOTOPLETHYSMOGRAPHY SENSOR

(71) Applicants: David R. Hall, Provo, UT (US); Dan Allen, Springville, UT (US); Andrew Davis, Provo, UT (US); Daniel Hendricks, Provo, UT (US); Justin Robinson, Provo, UT (US)

(72) Inventors: David R. Hall, Provo, UT (US); Dan Allen, Springville, UT (US); Andrew Davis, Provo, UT (US); Daniel Hendricks, Provo, UT (US); Justin Robinson, Provo, UT (US)

( * ) Notice: Subject to any disclaimer, the term of this patent is extended or adjusted under 35 U.S.C. 154(b) by 153 days.

(21) Appl. No.: 15/284,936

(22) Filed: Oct. 4, 2016

(65) Prior Publication Data

US 2018/0092602 A1    Apr. 5, 2018

(51) Int. Cl.

| | |
|---|---|
| A61B 5/02 | (2006.01) |
| A61B 5/00 | (2006.01) |
| A61B 5/026 | (2006.01) |
| A61B 5/0205 | (2006.01) |
| A47K 13/24 | (2006.01) |
| A61B 5/024 | (2006.01) |
| A61B 5/11 | (2006.01) |
| A61B 5/021 | (2006.01) |
| A61B 5/1455 | (2006.01) |
| A61B 5/053 | (2006.01) |
| A61B 90/00 | (2016.01) |

(52) U.S. Cl.
CPC .......... *A61B 5/6891* (2013.01); *A47K 13/24* (2013.01); *A61B 5/0205* (2013.01); *A61B 5/0261* (2013.01); *A61B 5/02125* (2013.01); *A61B 5/02427* (2013.01); *A61B 5/0535* (2013.01); *A61B 5/1102* (2013.01); *A61B 5/14552* (2013.01); *A61B 2090/064* (2016.02); *A61B 2090/065* (2016.02); *A61B 2503/08* (2013.01); *A61B 2503/12* (2013.01); *A61B 2505/07* (2013.01); *A61B 2560/0462* (2013.01); *A61B 2560/0468* (2013.01); *A61B 2562/046* (2013.01)

(58) Field of Classification Search
CPC ......... A61B 5/00; A61B 5/0205; A61B 5/026; A61B 2560/0462; A61B 2090/064; A61B 2090/3614; A61B 5/1102; A61B 2562/0238; A61B 2562/046; A61B 5/02125; A61B 5/14552; A61B 5/053; A61B 5/02427; A61K 13/24
See application file for complete search history.

(56) References Cited

U.S. PATENT DOCUMENTS

| | | | |
|---|---|---|---|
| 2012/0203077 A1* | 8/2012 | He ..................... | A61B 5/02055 600/301 |
| 2013/0030267 A1* | 1/2013 | Lisogurski .......... | A61B 5/0478 600/324 |
| 2016/0015276 A1* | 1/2016 | Strauss ................ | A61B 5/0537 600/301 |

(Continued)

*Primary Examiner* — Eric J Messersmith

(57) ABSTRACT

A synthetic aperture photoplethysmography (PPG) sensor is disclosed. A group or matrix of contiguous PPG sensors located on a toilet seat are conditionally combined based on sensor measurements. Conditional combinations may be based on timing data and signal-to-noise ratio data of each of the PPG measurements. Measurements associated with the conditional combinations are then used to determine a cardiac function of a toilet user.

13 Claims, 10 Drawing Sheets

(56) References Cited

U.S. PATENT DOCUMENTS

2016/0374619 A1* 12/2016 Borkholder .......... A61B 5/6891
  600/301
2017/0360316 A1* 12/2017 Gu ..................... A61B 5/02433

* cited by examiner

SYNTHETIC APERTURE PHOTOPLETHYSMOGRAPHY SENSOR

TECHNICAL FIELD

This invention relates generally to a field of heart health data collection devices, and more specifically to determining a cardiac function of a toilet seat user using photoplethysmography.

BACKGROUND

Heart health data is collected by healthcare professionals and patients for the purpose of understanding and improving patients' health. It is common for physicians to collect this data utilizing photoplethysmography (PPG) measurements. When necessary, patients collect PPG measurements themselves.

One problem with PPG measurement collection is that it can be tedious, requiring a patient's time and the time of his or her physician. It may also be difficult to collect accurate data when PPG measurements are sensitive to movement of the patient. Another problem is that data which is collected at one moment in time may be representative of only that moment. In general, when a patient is out of a care facility, PPG measurement collection may not be as frequent or as regular as would be desired to obtain more comprehensive heart health data.

SUMMARY OF THE INVENTION

A method of conditionally combining photoplethysmography (PPG) measurements is disclosed that overcomes or improves upon the limitations discussed above. In general, a synthetic aperture photoplethysmography (PPG) sensor is disclosed. A group of contiguous PPG sensors located on a toilet seat are conditionally combined based on sensor measurements. Conditional combinations may be based on timing data or signal-to-noise ratio data of each of the PPG measurements. Measurements associated with the conditional combinations are then used to determine a cardiac function of a toilet user. Averaging of one or more of the conditional combinations may be used to determine the cardiac function of a toilet user. One or more conditional combinations may be determined (grouping of sensor measurements) at least partially based on an intensity level of received light at the PPG sensors. One or more of the one or more conditional combinations are determined at least partially based on an intensity level change of received light at the PPG sensors over a predetermined time interval. Ballistocardiography (BCG) measurements from a BCG sensor located in the toilet seat and/or bio-impedance measurements from electrodes in the toilet seat may be obtained and used to determine a predetermined time interval filter for filtering changes in PPG sensor readings within the predetermined time interval of each PPG sensor. Conditional combinations or groupings of PPO sensors based on similar deltas or change amounts within the predetermined time interval may be used to obtain optimal PPG sensor groupings. The optimal groupings may be further averaged or the first PPG sensor measurement which arrived first-in-time may be selected and used to determine a cardiac function of the toilet user. Obtaining BCG measurements may comprise measuring a changing weight of the toilet seat user over time with the one or more force sensors. A group of contiguous PPG sensors may be arranged in a two-dimensional array. The contiguous PPG sensors may comprise photodiode devices, charge-coupled devices (CCDs), active-pixel sensors, or complementary metal-oxide-semiconductor (CMOS) sensors. The contiguous PPG sensors may comprise light emitting diodes or laser diodes. The contiguous PPG sensors may comprise both light transmitters and light receivers. Combining the PPG measurements may comprise selectively averaging two or more of the PPG measurements. Two or more of the PPG measurements may be selected based on a signal-to-noise ratio threshold and a data timing threshold. One or more conditional combinations may be determined by choosing a conditional combination of the one or more conditional combinations which has a first arrival in-time compared to the other combinations or individual sensor measurements of the first arrival combination. The cardiac function may comprise blood oxygen level, heart rate, blood pressure, blood flow rate, pulse transit time, or a combination thereof. Bio-impedance measurements may be obtained from bio-impedance electrodes on the toilet seat of a toilet. Timing data may include timing data associated with the bio-impedance measurements. Toilet seat may comprise one or more fiber optic lines or bundles of optical fibers. The optical fibers may connect to a plurality of light emitting diodes and at least one optical detector.

The general embodiment described above saves time and is more convenient for patients and physicians, because PPG measurements may be collected automatically in patients' residences or in clinics or hospitals. Collecting PPG measurements from contiguous PPG sensors facilitates more accurate data, since the PPG measurements are combined into less movement-sensitive conditional combinations. Positioning errors due to a user's position on a toilet seat are also reduced or eliminated. Positioning errors due to blood reflection positioning on a PPG sensor are reduced or eliminated. Weak reflection and noise due to a small sensor aperture are eliminated. With the PPG sensors being located on a toilet seat, PPG measurements may be collected regularly from a patient within his or her residence. This enables more regular and comprehensive heart health data.

In one embodiment, a method of conditionally combining PPG measurements is disclosed which includes obtaining PPG measurements, combining the PPG measurements into conditional combinations, and using the conditional combinations to determine cardiac function of a toilet seat user. The PPG measurements are obtained from a group of contiguous PPG sensors located on a toilet seat. The conditional combinations are combined dependent on timing data and signal-to-noise ratios corresponding to each of the PPG measurements.

BRIEF DESCRIPTION OF THE DRAWINGS

A more particular description of the invention briefly described above is made below by reference to specific embodiments. Several embodiments are depicted in drawings included with this application, in which.

DETAILED DESCRIPTION

A detailed description of the claimed invention is provided below by example, with reference to embodiments in the appended figures. Those of skill in the art will recognize that the components of the invention as described by example in the figures below could be arranged and designed in a wide variety of different configurations. Thus, the detailed description of the embodiments in the figures is merely representative of embodiments of the invention, and is not intended to limit the scope of the invention as claimed.

In some instances, features represented by numerical values, such as dimensions, mass, quantities, and other properties that can be represented numerically, are stated as approximations. Unless otherwise stated, an approximate value means "correct to within 50% of the stated value." Thus, a length of approximately 1 inch should be read "1 inch+/−0.5 inch."

Aspects of the present invention are described herein with reference to flowchart illustrations and/or block diagrams of methods, apparatus (systems), and computer program products according to embodiments of the invention. Those of skill in the art will understand that each block of the flowchart illustrations and/or block diagrams, and combinations of blocks in the flowchart illustrations and/or block diagrams, may be implemented by computer readable program instructions. Additionally, those of skill in the art will recognize that the system blocks and method flowcharts, though depicted in a certain order, may be organized in a different order and/or configuration without departing from the substance of the claimed invention.

Figure 1:
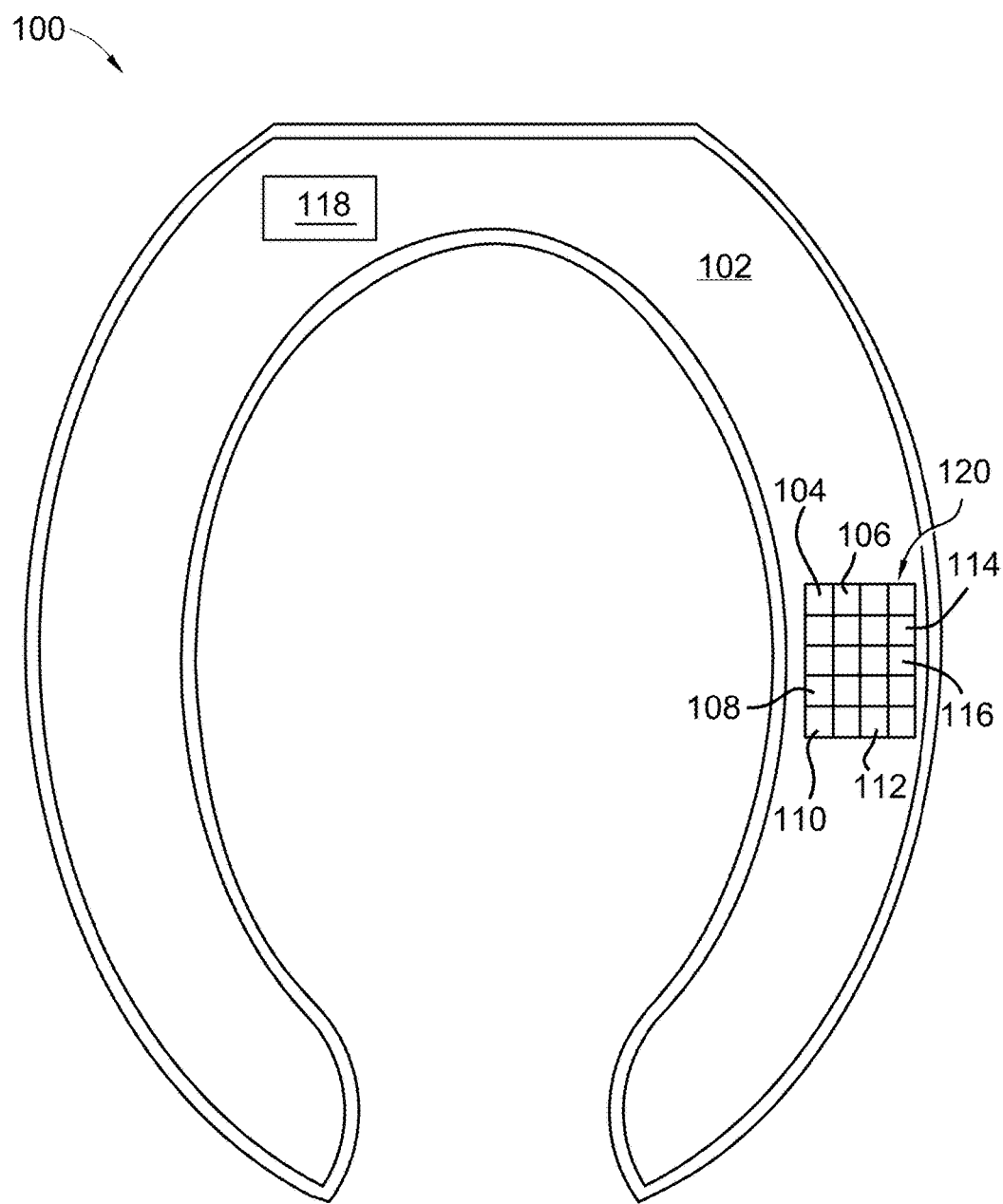
FIG. 1 shows a toilet seat with contiguous PPG sensors in accordance with an embodiment of the invention.

FIG. 1 depicts a top view 100 of a toilet seat 102 having an array of photoplethysmography (PPG) sensors 120. The PPG sensor array may form a two-dimensional or matrix array as shown in FIG. 1. The matrix of PPG sensors may have any number of columns and rows and be placed at any location along the toilet seat. Each of the PPG sensors in the array comprise at least a light transmitter and a light receiver. Light transmitters may be light emitting diodes or laser diodes. Light receivers may be photodiodes, charge-coupled devices (CCDs), active-pixel sensors, or complementary metal-oxide-semiconductor (CMOS) sensors. Toilet seat 102 includes a plurality of photoplethysmography (PPG) sensors 120 in a matrix or group of contiguous PPG sensors. The Group of PPG sensors is located on toilet seat 102 being recessed in the surface allowing a substantially planer top surface where a user of the toilet may sit and contact skin while using toilet seat 102. A method for utilizing toilet seat 102 to conditionally combine PPG measurements is described. The method includes obtaining PPG measurements from PPG sensor group 120, combining the PPG measurements into conditional combinations, and using the conditional combinations to determine cardiac function of a toilet seat user. Combining the PPG measurements into conditional combinations may be dependent on timing data and/or signal-to-noise ratios corresponding to each of the PPG measurements. For instance, PPG sensor array 120 includes 20 PPG sensors. If a user were to cover all or some of the 20 PPG sensors, an ideal sensor would output an analog intensity value changing in time based on blood profusion through the leg, thigh, and/or buttocks area as a result of a user's heart beating. Some PPG sensors may measure a high intensity which does not change over time proportional to a heartbeat or blood flow, have a low signal-to-noise ratio, or have a high or low intensity value which does not change overtime proportional to a heartbeat or blood flow. Direct reflections from a source light caused by skin surface topology, lotions, tattoos, or inclusions or protrusions on the skins surface may add to noise and keep blood profusion light scattering from modulating light detectors in some of the PPG sensors. Such sensors may be grouped together. Other sensors may have a low or high intensity which does not change due to ambient light conditions or lack of light transmitted back the light detectors in the PPG sensors, these may be grouped in another group. Sensors with data representative of a user's heart beat may be grouped in another group. Sensor in a group may be further filtered based on intensity levels of signals and timing of signals. One or more signals representative of a user's heart beat may be chosen as a usable PPG signal or averaged with another signal to form a usable PPG signal. Sensors with low or high intensity levels which do not change relative to a user's heart beat may have light sources turned off to reduce noise to other sensors with usable signals. Sensors not touching skin of a user may also have light sources turned off.

In some embodiments, toilet seat 102 includes a controller 118. Controller 118 may be coupled via a wire or wirelessly to PPG sensors 120. Controller may include memory, one or more processors, wireless and wired transceivers and be operably connected to PPG array sensors. Controller 118 may communicate with remote computers and user devices over the Internet or through direct local connections. Controller 118 may receive PPG measurements as well as timing data, and may store them in memory for later use. The controller may be coupled to a power source such as a wall outlet, batteries, etc. Additionally, the controller may control power flow or data communications to and from PPG array sensors 120.

In some further embodiments, the controller combines the PPG measurements into the conditional combinations and may use the conditional combinations in determining values for metrics relating to cardiac health. The previously mentioned metrics may include blood-oxygen saturation levels, systolic and diastolic pressures, frequency of premature ventricular contraction, heart beat rate, pulse transit time, pulse arrival time, pulse wave velocity, systolic amplitude, pulse width, pulse area, arterial stiffness index, etc. The preceding metrics are well known in the art, as a person having skill in the art may appreciate.

PPG sensors 120 may each include a photodetector. One or more of the PPG sensors may include light transmitters to illuminate tissue and detect blood profusion of the toilet user, in conjunction with the photodetectors which are used to measure small variations in light intensity associated with changes in blood vessel volume. Increase in blood volume indicates decrease in light intensity and vice versa.

In some embodiments, toilet seat 102 may include a wireless transceiver. The wireless transceiver may communicate with a peripheral device which may, in turn, combine the PPG measurements into the conditional combinations and use them to determine cardiac health metrics, as described above. The peripheral device may be any of a variety of devices, including a laptop, a smart phone, a cloud server, etc.

In some embodiments, toilet seat 102 includes pressure sensors. When the toilet seat user sits on toilet seat 102 the pressure sensors may send a signal to a controller and/or the PPG sensors 120. Subsequently, PPG sensors 120 may obtain PPG measurements.

In the depicted embodiment, group 120 of contiguous PPG sensors is arranged in a two-dimensional array.

Figure 2:
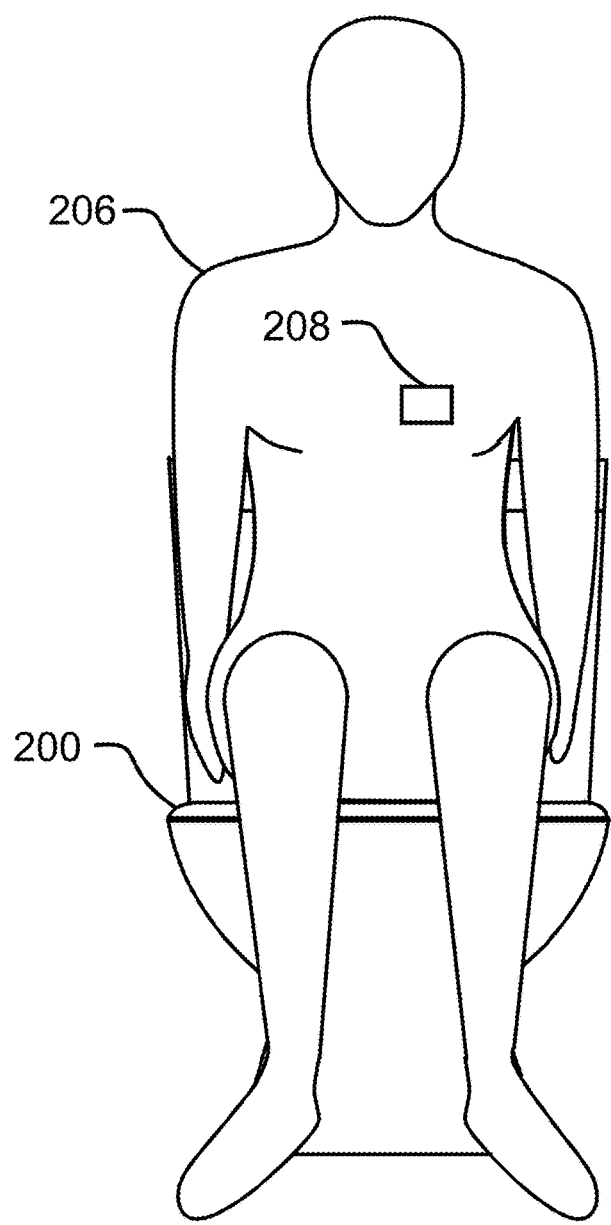
FIG. 2 shows a user on a toilet in accordance with an embodiment of the invention.

FIG. 2 depicts a front view of a user using a toilet. Toilet seat 200 includes a group of contiguous PPG sensors (as depicted in FIG. 1). Toilet seat user 206 has ballistocardiography (BCG) sensor 208 attached to him or her. A method of conditionally combining PPG measurements is described. The method includes obtaining PPG measurements from the PPG sensors located on toilet seat 200 and conditionally combining them. Additionally, the method includes obtaining BCG measurements from BCG sensor 208.

The BCG measurements may be used with the PPG measurements to determine pulse transit time (PTT). As is known in the art, PTT is dependent on blood pressure, making it easy to use to determine blood pressure of user 206.

Figure 3:
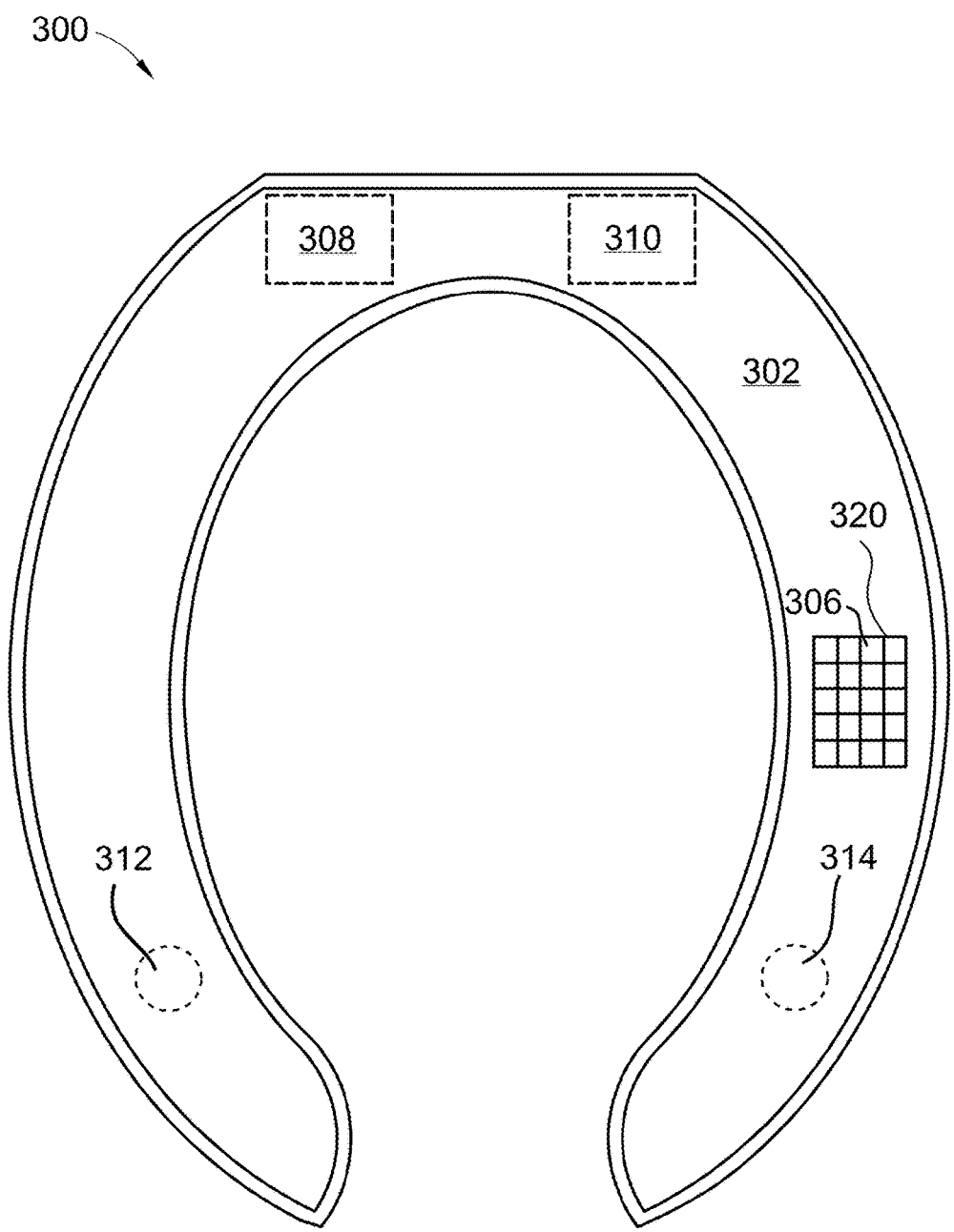
FIG. 3 shows a toilet seat with contiguous PPG sensors in accordance with an embodiment of the invention.

FIG. 3 depicts an embodiment with a BCG sensor. Toilet seat 302 includes a group 320 of contiguous PPG sensors 320 and ballistocardiography (BCG) sensors 308, 310, 312 and 314. BCG sensors 308, 310, 312 and 314 are located in toilet seat 302. In some embodiments, BCG sensors 308, 310, 312 and 314 are force sensors. BCG sensors 308, 310, 312 and 314 may be used to detect a toilet user's heart beat and provide a timing filter for PPG sensors 320. Timing signal of BCG sensors 308, 310, 312 and 314 may be used to form conditions of conditional combinations of PPG sensors 320.

A method of conditionally combining PPG measurements is described. The method includes obtaining PPG measurements from group 320, combining the PPG measurements into conditional combinations, and using the conditional combinations to determine cardiac function of a toilet seat user. In some other embodiments, wherein BCG sensor 308 is a force sensor, obtaining PPG measurements includes measuring a weight of the toilet seat user with the force sensor. Subsequently the method includes adjusting intensities of light emitted by light transmitters corresponding to the contiguous PPG sensors, dependent on the weight of the toilet seat user.

Light transmitters of PPG sensors 320 may emit light with varying intensities in an attempt to find useable PPG signals. Toilet users with different weight may need more or less light intensity to detect usable PPG signals.

In some embodiments, when toilet weight is detected by BCG sensors 308, 310, 312 and 314 triggering of PPG sensors 320 may occur. When weight is removed from toilet seat 302 PPG sensors 302 may deactivate. In some embodiments, PPG sensors 302 deactivate fifteen seconds after a weight has been removed from toilet seat 300, as sensed by BCG sensor 308. In some further embodiments, PPG sensors 302 deactivate immediately if toilet seat 300 is raised, as sensed by orientation sensor 310.

Figure 4:
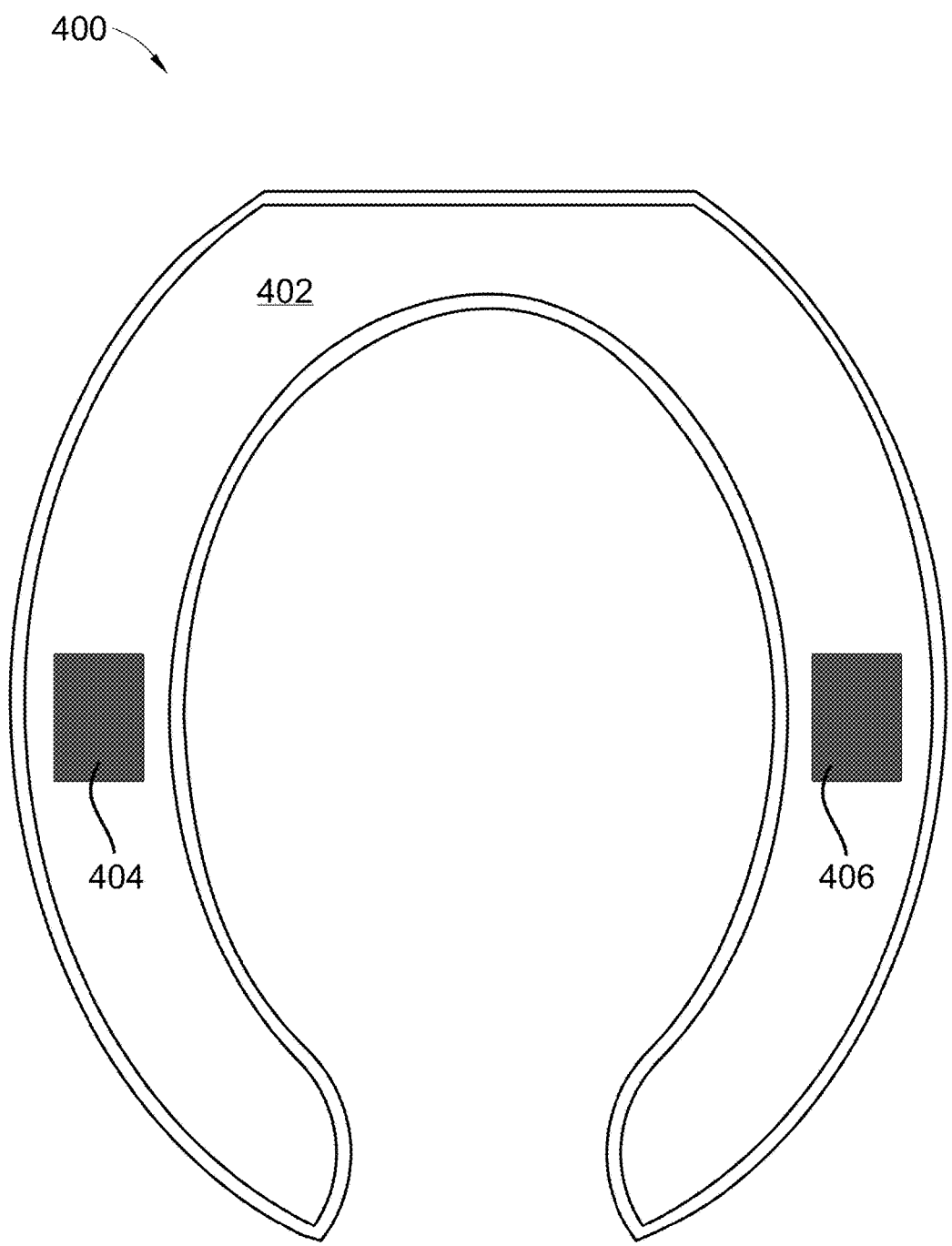
FIG. 4 shows a toilet seat with contiguous PPG sensors in accordance with an embodiment of the invention.

FIG. 4 depicts an embodiment with arrays of PPG sensors 404 and 406 on each side of toilet seat 402. Toilet seat 402 includes groups 404 and 406 of contiguous PPG sensors. Due to the contiguity of PPG sensors of groups 404 and 406, PPG sensors may obtain differing PPG measurements which, when combined, may be used to determine cardiac function of a toilet seat user.

Figure 5:
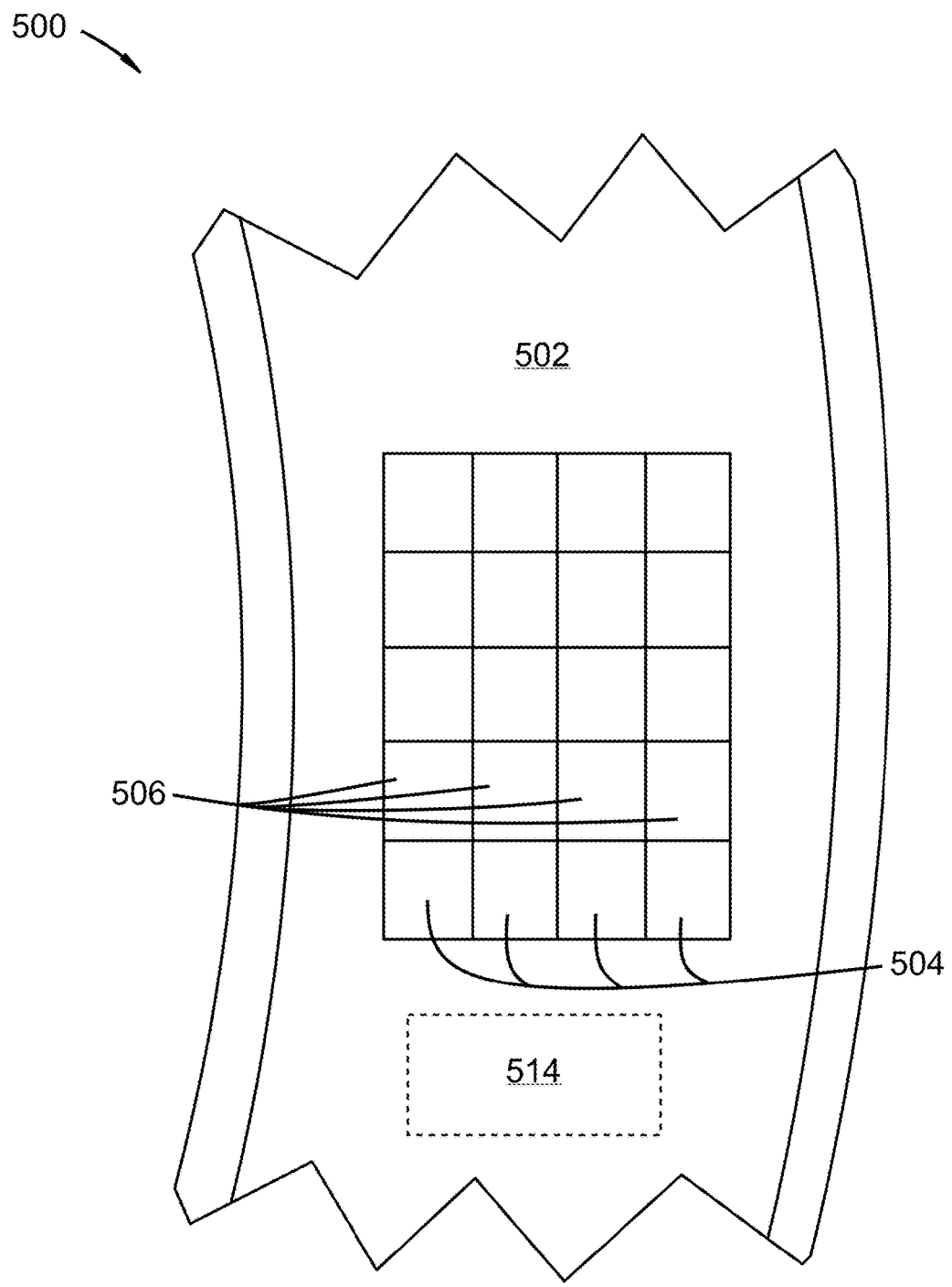
FIG. 5 shows a top view of a portion of toilet seat with a close view of contiguous PPG sensors in accordance with an embodiment of the invention.

FIG. 5 depicts a section of a toilet seat having PPG sensors. Toilet seat 502 includes a group 504 of contiguous PPG sensors. A method of conditionally combining PPG measurements is described. The method includes obtaining PPG measurements from PPG sensors and combining the PPG measurements into conditional combinations. The conditional combinations are combined dependent on timing data and signal-to-noise ratios corresponding to each of the PPG measurements. Combining the PPG measurements includes averaging timing data corresponding to the PPG measurements.

In some embodiments, toilet seat 502 includes controller 514 which is connected to PPG sensors. When a PPG measurement is obtained from one of PPG sensors 504, 506, it is read by controller 514. Controller 514 then stores the PPG measurement in volatile and/or static memory. In some embodiments, controller 514 may assign timing data to PPG measurements corresponding to a time the PPG measurement was received. In some other embodiments, controller 514 may assign timing data to PPG measurements corresponding to a time offset from when the PPG measurement was received. In some yet other embodiments, the PPG sensor corresponding to the PPG measurement assigns timing data when the PPG measurement is obtained and passes that timing data to controller 514.

In some embodiments averaging the timing data corresponding to the PPG measurements includes determining an arithmetic mean of the timing data; it may also include storing the arithmetic mean timing data to be used to help determine cardiac function of a toilet seat user.

Depending on signal-to-noise ratios of each PPG measurement, controller 514 may accept some PPG measurements to be used in averaging timing data corresponding to the PPG measurements. Depending on signal-to-noise ratios of each PPG measurement, controller 514 may also reject some PPG measurements to be used in averaging timing data corresponding to the PPG measurements. For example, in some embodiments a first sensor, a second sensor, a fifth sensor, a sixth sensor, and a ninth sensor of PPG sensors 504 and 506 have relatively low signal-to-noise ratios. Controller 514 may reject PPG measurements corresponding to aforementioned sensors and accept all other PPG measurements with sufficiently high signal-to-noise ratios.

In some embodiments, averaging timing data includes computing a weighted average of the timing data corresponding to the PPG measurements. The sum of the products of timing data times and corresponding weight coefficients are equal to one. I.e. $1=\Sigma_{i=1}^{N}(B_i t_i)$, where $B_i$ is an ith weight coefficient and $t_i$ is a corresponding ith timing data time. The weight coefficients are determined as functions of corresponding signal-to-noise ratios, relative sensor placement of PPG sensors 504 and 506, and relative phase shift of timing data. Each weight coefficient may vary as a function of signal-to-noise ratio of its corresponding multiplicand time. Each weight coefficient may also vary as a function of its corresponding sensor placement with respect to other PPG sensors 504 and 506. Additionally, each coefficient may vary as a function of relative phase shift of its corresponding multiplicand time. I.e. $B_i = f(SNR, x, y, t_j, I_k)$, where SNR is a signal-to-noise ratio of a corresponding PPG measurement, x and y are coordinates which define position of a corresponding sensor of PPG sensors 504 and 506, $t_j$ is an array of times corresponding to timing data of a sensor of PPG sensors 504 and 506, and $I_k$ is an array of light intensities corresponding to PPG measurements.

Figure 6:
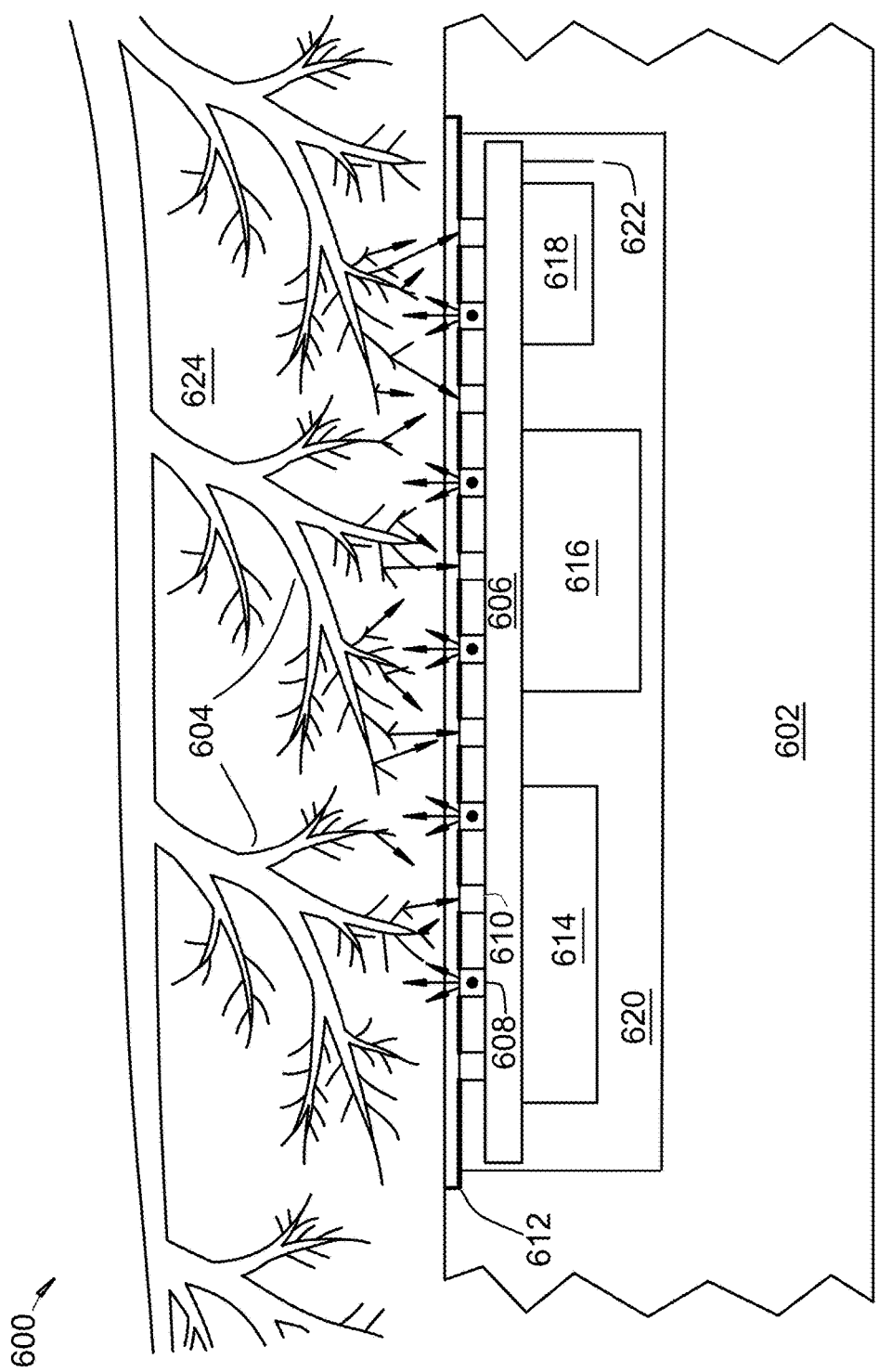
FIG. 6 shows cross-sectional view of a toilet seat, contiguous PPG sensors, and a user's leg in accordance with an embodiment of the invention.

FIG. 6 depicts a cross-sectional view of a PPG sensor array in toilet seat 602 with a user's thigh tissue 624 contacting the top of the PPG sensor array in accordance with an embodiment of the invention. The sensor array includes light sources 608 and light detectors 610 forming a matrix of contiguous PPG sensors on a surface of toilet seat 602. Circuit board 606 has light sources 608 and light detectors 610 operably connected to a top side of circuit board 606 and processor/controller/memory 614, battery 616, transceiver 618, and antenna 622 operably connected to a bottom side of circuit board 606. The PPG sensor array may be disposed in a recess such as 620 in toilet seat 602. Other circuit and wiring arrangements are possible. Cover glass 612 provides a smooth flat transparent surface for a user's thigh 624 to rest on while also providing protection to the PPG sensor array. Light sources 608 and 610 and circuit board 606 may be attached to cover glass 612 using glue or other adhesive material disposed between light sources 608 and light detectors 610. Cover glass 612 and circuit board 606 may be removed as a single module and battery 616 may be replaced as necessary. This may be accomplished with a suction cup attached to the top surface of the cover glass and lifting the PPG module out of recess 620, a push button releasing the PPG module, or any other know method of removing modules and replacing batteries. Battery 616 may be a rechargeable battery. Recharging may occur by non-contact inductive charger built into a toilet seat lid. Optional power wires may pass though the toilet seat hinges to a power source in the toilet or remote to the toilet and the batteries of the PPG array may be optional.

The PPG sensor array shown is a wireless, self-contained, PPG measurement system which communicates wirelessly with one or more user devices, computers, servers, and/or databases. Antenna 622 and transceiver 618 may work on one or more frequencies including Bluetooth, WiFi, SureFi, Zigbee, GSM, or other known home automation protocols and frequencies. Controller 614 may include memory, one or more processors, A/D and D/A converters, and programming necessary to obtain and provide PPG sensor array measurements to remote devices and users.

As a user's thigh 624 contacts toilet seat 602, weight sensors in toilet seat 602 may trigger a signal to be sent to antenna 622 waking up circuit 606. Light sources 608 may then transmit light toward thigh tissue 624. As a user's heart beats, arterioles 604 in the subcutaneous tissue distend and change color the of the surrounding tissue due to profusion of blood in the capillaries. Arterioles 604 and capillaries may be closer to some of the light sources 608 and farther from other light sources 608. As light is reflected back to light sensors 610, some of the sensors will obtain changing intensity information related to the cardiac cycle of the toilet user. A processor and memory in controller 614 obtain data from light sensors 610 and look for data which can be grouped together based on timing of the data, intensity of the data, and changes in the data over a predetermined time period. The predetermined time period may be obtained from a BCG reading of the user, a bio-impedance reading of the user, or from one or more sensors of the PPG array. The predetermined time period may be associated with a heartbeat of the toilet user. When controller 614 determines which sensors are receiving valid data, light sources associated with invalid data sensors may be turned off or intensities of the light sources may be varied to try to achieve valid data. For instance, if a light sensor 610 is not receiving data associated with a cardiac cycle of the toilet user then the intensity of adjacent light sources may be increased, decreased, or turned off to try to obtain valid data and/or increase signal-to-noise ratios of nearby light sensors 610 of the matrix array.

Figure 7:
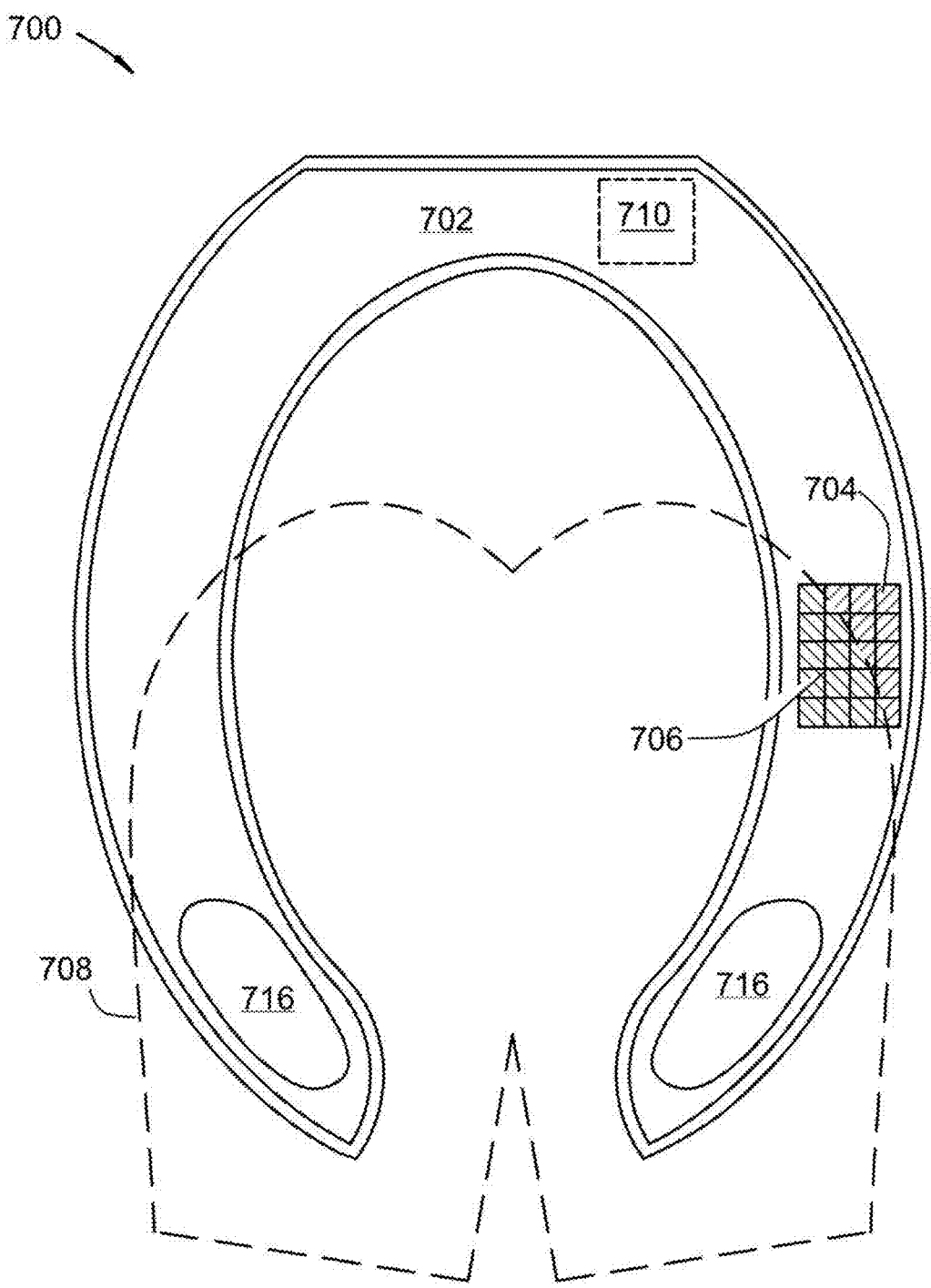
FIG. 7 shows a top view with a user sitting on a toilet seat with contiguous PPG sensors in accordance with an embodiment of the invention.

FIG. 7 depicts an embodiment with bio-impedance electrodes on a toilet seat. Toilet seat 702 includes PPG sensors 706 and bio-impedance electrodes 716. A method of conditionally combining PPG measurements is described. The method includes obtaining PPG measurements from PPG sensors 706 and obtaining bio-impedance measurements from bio-impedance electrodes 716. In some embodiments, the bio-impedance measurements may be used in determining heart beats of a toilet seat user. PPG measurements may be compared to bio-impedance measurements in order to determine pulse arrival times or pulse transit times. PPG sensors may be filtered or conditionally combined based on a timing pattern obtained from bio-impedance measurements.

In FIG. 7, a user 708 is sitting on a PPG sensor array. PPG sensors 706 are contacting a thigh of user 708 and PPG sensor 704 are exposed. Exposed sensors 704 may be combined into a conditional combination based on none changing intensity received by the light sensors associated with PPG sensors 704. Light sources associated with uncovered sensors 704 may be turned off in a fraction of a second after being turned on due to a determination of uncovered sensors.

The method further includes combining the PPG measurements into conditional combinations, and using the conditional combinations and the bio-impedance measurements to determine cardiac function of a toilet seat user. The cardiac function to be determined may include blood-oxygen saturation levels, systolic and diastolic pressures, frequency of premature ventricular contraction, heart beat rate, pulse transit time, pulse arrival time, pulse wave velocity, systolic amplitude, pulse width, pulse area, and arterial stiffness index. The cardiac function to be determined may additionally include comparisons and changes of blood-oxygen saturation levels, systolic and diastolic pressures, frequency of premature ventricular contraction, heart beat rate, pulse transit time, pulse arrival time, pulse wave velocity, systolic amplitude, pulse width, pulse area, and arterial stiffness index.

Some PPG sensors may measure a high intensity which does not change over time proportional to a heartbeat or blood flow, have a low signal-to-noise ratio, or have a high or low intensity value which does not change overtime proportional to a heartbeat or blood flow. Direct reflections from a source light caused by skin surface topology, lotions, tattoos, or inclusions or protrusions on the skins surface may add to noise and keep blood profusion light scattering from modulating light detectors in some of the PPG sensors. Such sensors may be grouped together. Other sensors may have a low or high intensity which does not change due to ambient light conditions or lack of light transmitted back the light detectors in the PPG sensors, these may be grouped in another group. Sensors with data representative of a user's heart beat may be grouped in another group. Sensor in a group may be further filtered based on intensity levels of signals and timing of signals. One or more signals representative of a user's heart beat may be chosen as a usable PPG signal or averaged with another signal to form a usable PPG signal. Sensors with low or high intensity levels which do not change relative to a user's heart beat may have light sources turned off to reduce noise to other sensors with usable signals. Sensors not touching skin of a user may also have light sources turned off.

Figure 8:
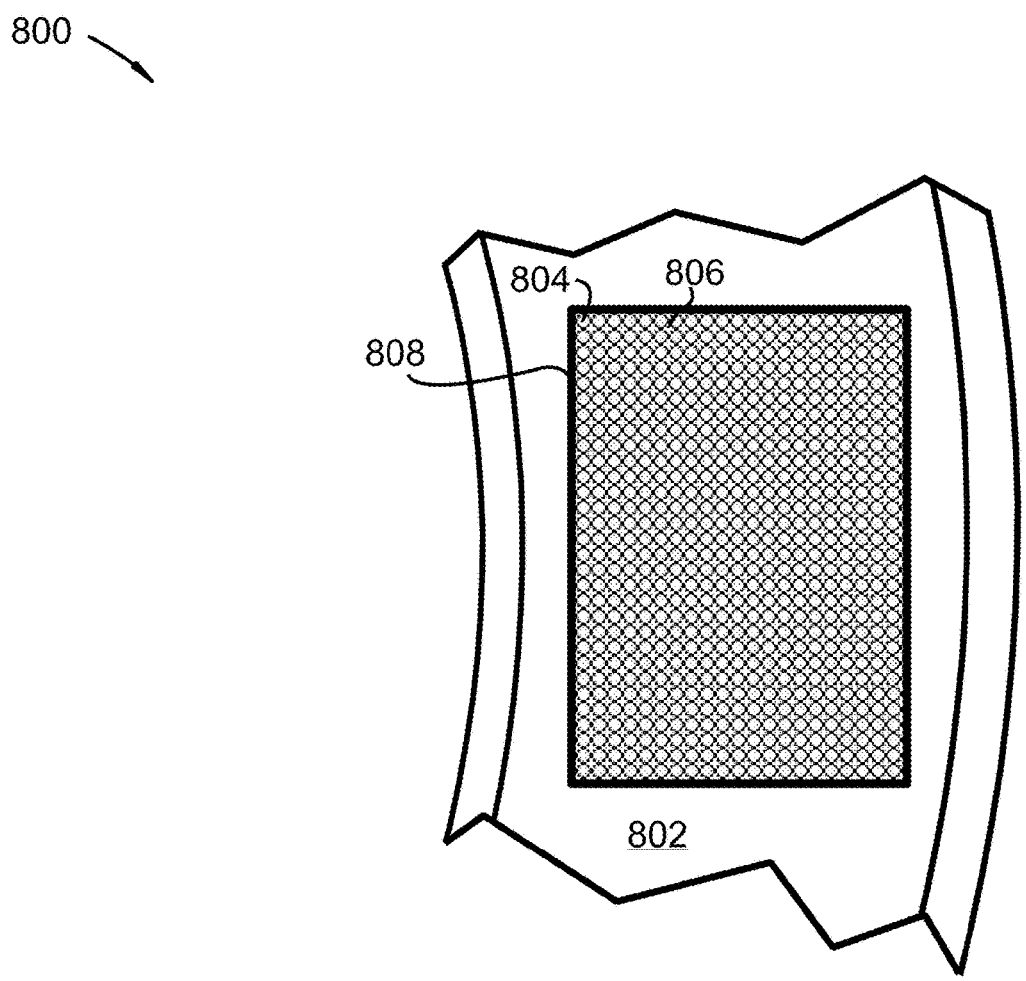
FIG. 8 shows a top view of a portion of toilet seat with a close view of contiguous PPG sensors in accordance with an embodiment of the invention.

FIG. 8 depicts an embodiment with hundreds of light sources 806 and hundreds of light detectors 804. PPG array 808 includes light sources 806 and light detectors 804. A method of conditionally combining PPG measurements is described. The method includes obtaining PPG measurements from the PPG sensors and combining the PPG measurements into conditional combinations. In some embodiments, optical light sources 806 are combined in groups of lesser numbers than that of all of light sources 806. A processor coupled to light sources 806 and 808 may turn of light sources not need or producing unusable data and manipulate other light sources to obtain the best data possible. For instance, a processor may selectively increase or decrease light intensity and/or light patterns of covered light sources to obtain high quality PPG data. If an observer were to watch the PPG measurement process, he or she may observe lots of blinking LEDs or laser LEDs until the best usable signal was obtained. Light sensors 804 may also be used or not used based on data and processor grouping of data. Select sensors 804 may be combined in a region or area to form a single large area light sensor for data processing purposes. A processor may determine which of the light sensors are receiving usable data and combine these sensors in a large sensor by averaging the data received at these sensors into one larger sensor. Each group of optical sensors 804 may have their measurements passively or actively combined. For example, in some embodiments, for each of the groups, optical sensors 804 are simultaneously obtaining PPG measurements corresponding to one PPG sensor per group. In this way, combining the PPG measurements into conditional combinations may take place as a passive step in the method described above. Light sensors 804 and light sources 806 may be formed into geographic combinations and/or combinations based on received light sensor data. Additionally, in some further embodiments, after the passive step aforementioned, the method includes actively combining the PPG measurements into conditional combinations by way of a controller. In such embodiments, the method may include using the conditional combinations to determine cardiac function of a toilet seat user. Conditional combinations may be formed based on data received by each optical sensor 804 and/or by additional data received by BCG and/or bio-impedance readings.

Some PPG sensors may measure a high intensity which does not change over time proportional to a heartbeat or blood flow, have a low signal-to-noise ratio, or have a high or low intensity value which does not change overtime proportional to a heartbeat or blood flow. Direct reflections from a source light caused by skin surface topology, lotions, tattoos, or inclusions or protrusions on the skins surface may add to noise and keep blood profusion light scattering from modulating light detectors in some of the PPG sensors. Such sensors may be grouped together. Other sensors may have a low or high intensity which does not change due to ambient light conditions or lack of light transmitted back the light detectors in the PPG sensors, these may be grouped in another group. Sensors with data representative of a user's heart beat may be grouped in another group. Sensor in a group may be further filtered based on intensity levels of signals and timing of signals. One or more signals representative of a user's heart beat may be chosen as a usable PPG signal or averaged with another signal to form a usable PPG signal. Sensors with low or high intensity levels which do not change relative to a user's heart beat may have light sources turned off to reduce noise to other sensors with usable signals. Sensors not touching skin of a user may also have light sources turned off.

Figure 9:
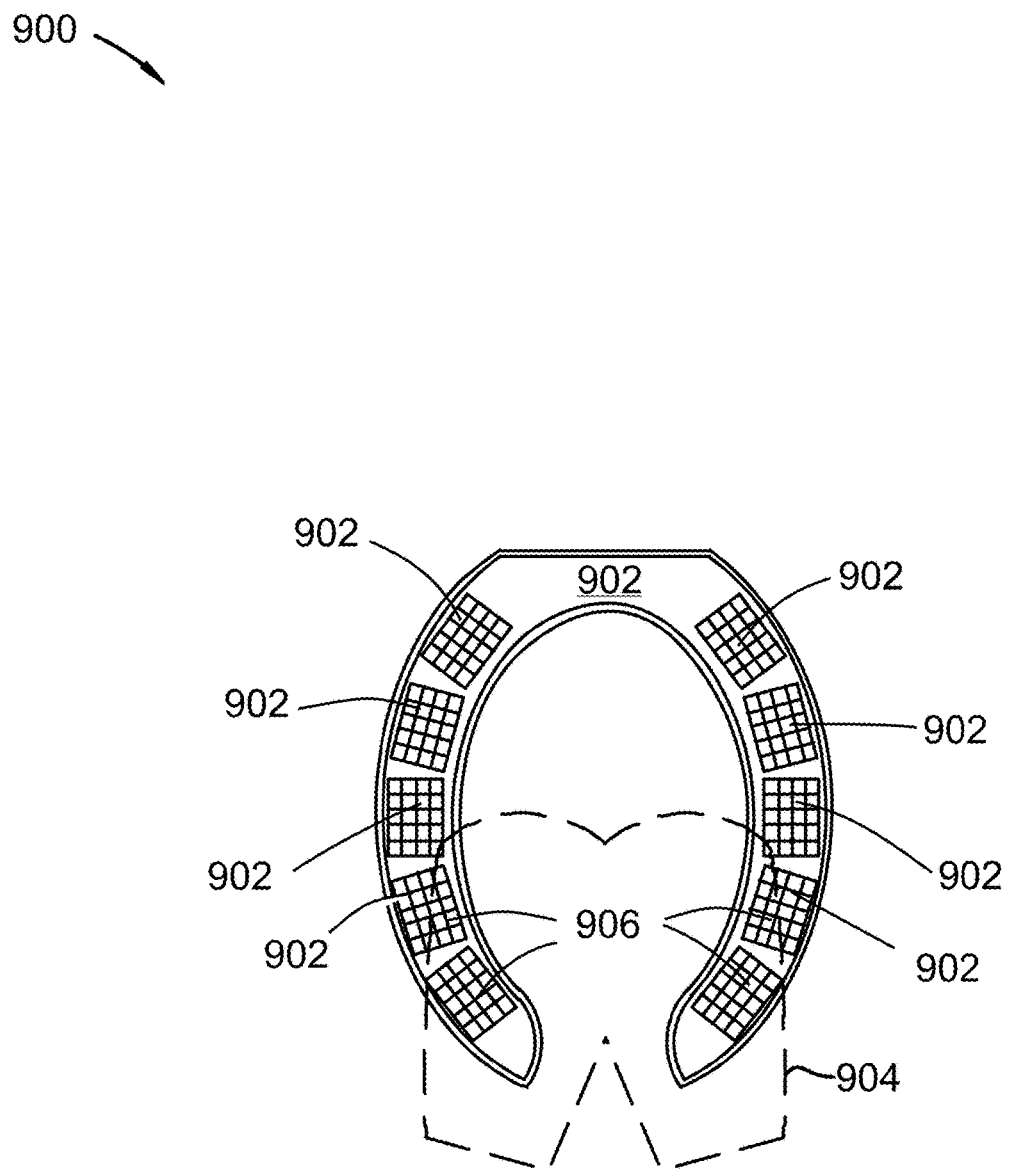
FIG. 9 shows a top view of a portion of toilet seat with a close view of contiguous PPG sensors in accordance with an embodiment of the invention.

FIG. 9 depicts an embodiment with user covered PPG sensor arrays 906 and uncovered PPG sensor arrays 902. User 906 may be a child or small adult with a relatively small toilet seat footprint. A method of conditionally combining PPG measurements is described. The method includes obtaining PPG measurements from the PPG arrays 906 and combining the PPG measurements into conditional combinations based on data received from each PPG sensor of the PPG arrays. A processor coupled to PPG arrays 902 may turn of light sources not covered by user 904. A processor may selectively increase or decrease light intensity and/or light patterns of covered light sources in PPG arrays 906 to obtain high quality PPG data. If an observer were to watch the PPG measurement process, he or she may observe lots of blinking LEDs or laser LEDs until the best usable signal was obtained. Select PPG array sensors may be combined in a region or area to form a single large area light sensor for data processing purposes. A processor may determine which of the light sensors are receiving usable data and combine these sensors in a large sensor by averaging the data received at these sensors into one larger sensor. Each group of optical sensors in PPG array 906 may have their measurements passively or actively combined. Light sensors and light sources of PPG array 906 may be formed into geographic combinations and/or combinations based on received light sensor data. Additionally, in some further embodiments, after the passive step aforementioned, the method includes actively combining the PPG measurements into conditional combinations by way of a controller. In such embodiments, the method may include using the conditional combinations to determine cardiac function of a toilet seat user. Conditional combinations may be formed based on data received by each optical sensor in PPG array 906 and/or by additional data received by BCG and/or bio-impedance readings.

Some PPG sensors may measure a high intensity which does not change over time proportional to a heartbeat or blood flow, have a low signal-to-noise ratio, or have a high or low intensity value which does not change overtime proportional to a heartbeat or blood flow. Direct reflections from a source light caused by skin surface topology, lotions, tattoos, or inclusions or protrusions on the skins surface may add to noise and keep blood profusion light scattering from modulating light detectors in some of the PPG sensors. Such sensors may be grouped together. Other sensors may have a low or high intensity which does not change due to ambient light conditions or lack of light transmitted back the light detectors in the PPG sensors, these may be grouped in another group. Sensors with data representative of a user's heart beat may be grouped in another group. Sensor in a group may be further filtered based on intensity levels of signals and timing of signals. One or more signals representative of a user's heart beat may be chosen as a usable PPG signal or averaged with another signal to form a usable PPG signal. Sensors with low or high intensity levels which do not change relative to a user's heart beat may have light sources turned off to reduce noise to other sensors with usable signals. Sensors not touching skin of a user may also have light sources turned off.

Figure 10:
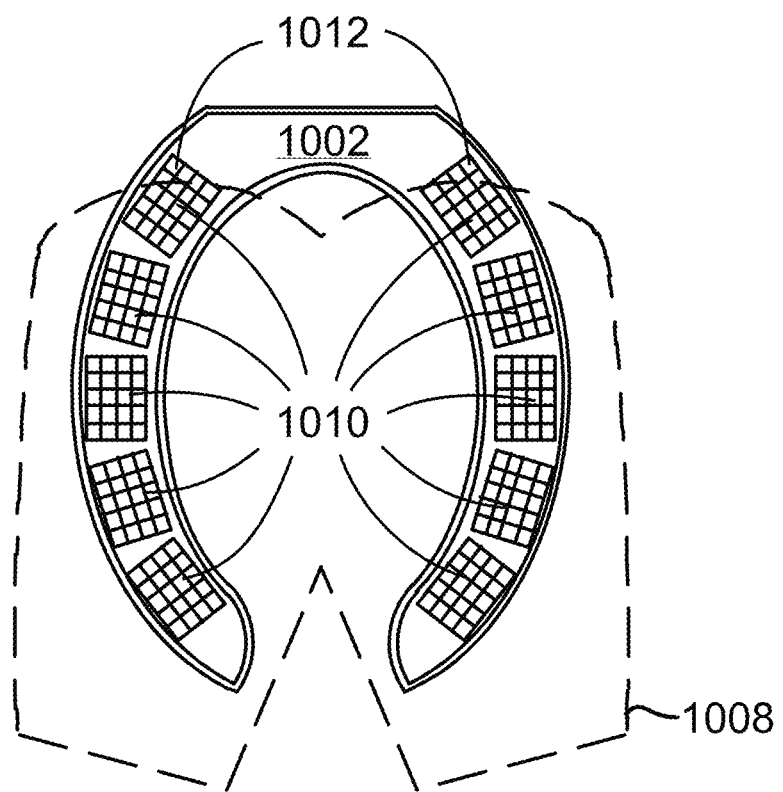
FIG. 10 shows a toilet seat with contiguous PPG sensors in accordance with an embodiment of the invention.

FIG. 10 depicts an embodiment with user covered PPG sensor arrays 1010 and uncovered PPG sensor arrays 1012. User 1008 may be a large adult with a relatively large toilet seat footprint. A method of conditionally combining PPG measurements is described. The method includes obtaining PPG measurements from the PPG arrays 1010 and combining the PPG measurements into conditional combinations based on data received from each PPG sensor of the PPG arrays. A processor coupled to PPG arrays 1012 may turn of light sources not covered by user 1008. A processor may selectively increase or decrease light intensity and/or light patterns of covered light sources in PPG arrays 1010 to obtain high quality PPG data. If an observer were to watch the PPG measurement process, he or she may observe lots of blinking LEDs or laser LEDs until the best usable signal was obtained. Select PPG array sensors may be combined in a region or area to form a single large area light sensor for data processing purposes. A processor may determine which of the light sensors are receiving usable data and combine these sensors in a large sensor by averaging the data received at these sensors into one larger sensor. Each group of optical sensors in PPG array 1010 may have their measurements passively or actively combined. Light sensors and light sources of PPG array 1010 may be formed into geographic combinations and/or combinations based on received light sensor data. Additionally, in some further embodiments, after the passive step aforementioned, the method includes actively combining the PPG measurements into conditional combinations by way of a controller. In such embodiments, the method may include using the conditional combinations to determine cardiac function of a toilet seat user. Conditional combinations may be formed based on data received by each optical sensor in PPG array 906 and/or by additional data received by BCG and/or bio-impedance readings.

Some PPG sensors may measure a high intensity which does not change over time proportional to a heartbeat or blood flow, have a low signal-to-noise ratio, or have a high or low intensity value which does not change overtime proportional to a heartbeat or blood flow. Direct reflections from a source light caused by skin surface topology, lotions, tattoos, or inclusions or protrusions on the skins surface may add to noise and keep blood profusion light scattering from modulating light detectors in some of the PPG sensors. Such sensors may be grouped together. Other sensors may have a low or high intensity which does not change due to ambient light conditions or lack of light transmitted back the light detectors in the PPG sensors, these may be grouped in another group. Sensors with data representative of a user's heart beat may be grouped in another group. Sensor in a group may be further filtered based on intensity levels of signals and timing of signals. One or more signals representative of a user's heart beat may be chosen as a usable PPG signal or averaged with another signal to form a usable PPG signal. Sensors with low or high intensity levels which do not change relative to a user's heart beat may have light sources turned off to reduce noise to other sensors with usable signals. Sensors not touching skin of a user may also have light sources turned off.

The systems and methods disclosed herein may be embodied in other specific forms without departing from their spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of conditionally combining photoplethysmography (PPG) measurements comprising:
providing a toilet, the toilet comprising a toilet seat, the toilet seat comprising a group of contiguous PPG sensors and at least one weight sensor, wherein the at least one weight sensor is in communication with the group of contiguous PPG sensors;
obtaining a weight detection from the at least one weight sensor when a user is seated on the toilet seat;
transmitting a signal from the weight sensor to the group of contiguous PPG sensors;
actuating the group of contiguous PPG sensors;
obtaining PPG measurements from the group of contiguous PPG sensors;
combining the PPG measurements into one or more conditional combinations based on timing data and signal-to-noise ratio data corresponding to each of the PPG measurements;
wherein the timing data is collected by a PPG sensor with low or high intensity values which change relative to a user's heart beating; and
using the one or more conditional combinations to determine a cardiac function of a toilet user.

2. The method of claim 1, further comprising averaging the one or more conditional combinations to determine the cardiac function of the toilet user.

3. The method of claim 1, wherein one or more of the one or more conditional combinations are determined at least partially based on an intensity level of received light at the PPG sensors.

4. The method of claim 1, further comprising obtaining ballistocardiography (BCG) measurements from a BCG sensor located in the toilet seat.

5. The method of claim 1, wherein the group of contiguous PPG sensors is arranged in a two-dimensional array.

6. The method of claim 1, wherein the contiguous PPG sensors comprise photodiode devices, charge-coupled devices (CCDs), active-pixel sensors, or complementary metal-oxide-semiconductor (CMOS) sensors.

7. The method of claim 1, wherein the contiguous PPG sensors comprise light emitting diodes or laser diodes.

8. The method of claim 1, wherein the contiguous PPG sensors comprise both light transmitters and light receivers.

9. The method of claim 1, wherein combining the PPG measurements comprises selectively averaging two or more of the PPG measurements.

10. The method of claim 1, wherein the one or more conditional combinations is determined by choosing a conditional combination of the one or more conditional combinations which has a first arrival in time.

11. The method of claim 1, wherein the cardiac function comprises blood oxygen level, heart rate, blood pressure, blood flow rate, pulse transit time, or a combination thereof.

12. The method of claim 1, wherein the toilet seat further comprises optical fibers.

13. The method of claim 12, wherein the optical fibers connect to a plurality of light emitting diodes and at least one optical detector.

* * * * *